United States Patent
Thakur et al.

(10) Patent No.: US 12,293,907 B2
(45) Date of Patent: May 6, 2025

(54) PHYSICAL-CHEMICAL PROPERTY SCORING FOR STRUCTURE ELUCIDATION IN ION SPECTROMETRY

(71) Applicant: Bruker Scientific LLC, Billerica, MA (US)

(72) Inventors: Rohan Thakur, Mountain View, CA (US); Robin Park, San Diego, CA (US)

(*) Notice: Subject to any disclaimer, the term of this patent is extended or adjusted under 35 U.S.C. 154(b) by 358 days.

(21) Appl. No.: 17/688,470

(22) Filed: Mar. 7, 2022

(65) Prior Publication Data

US 2022/0392757 A1    Dec. 8, 2022

Related U.S. Application Data

(60) Provisional application No. 63/208,801, filed on Jun. 9, 2021, provisional application No. 63/195,958, filed on Jun. 2, 2021.

(51) Int. Cl.
| | | |
|---|---|---|
| *H01J 49/00* | (2006.01) | |
| *G01N 33/68* | (2006.01) | |
| *G16C 20/20* | (2019.01) | |

(52) U.S. Cl.
CPC ...... *H01J 49/0036* (2013.01); *G01N 33/6848* (2013.01); *G16C 20/20* (2019.02)

(58) Field of Classification Search
CPC ........ H01J 49/00; H01J 49/02; H01J 49/0036; H01J 49/0027; H01J 49/0031;
(Continued)

(56) References Cited

U.S. PATENT DOCUMENTS

| | | | | |
|---|---|---|---|---|
| 6,393,367 B1 * | 5/2002 | Tang | ................... | H01J 49/0036 702/30 |
| 7,838,826 B1 | 11/2010 | Park | | |

(Continued)

FOREIGN PATENT DOCUMENTS

| | | |
|---|---|---|
| WO | 2001067485 A1 | 9/2001 |
| WO | 2004013635 A2 | 2/2004 |

(Continued)

OTHER PUBLICATIONS

Eng, Jimmy et al., "An Approach to Correlate Tandem Mass Spectral Data of Peptides with Amino Acid Sequences in a Protein Database", J. Am. Soc. Mass Spectrom. 1994, 5, 976-989.

(Continued)

*Primary Examiner* — Jason L McCormack
(74) *Attorney, Agent, or Firm* — Benoît & Côté Inc.

(57) ABSTRACT

Disclosed is a method of associating molecular structures with signal peaks in spectrometry data obtained from separation according to one or more physical-chemical properties, comprising, as the case may be repeatedly: providing one or more signal peaks in acquired spectrometry data being related to an experimental value of mobility or a related property; ascertaining one or more molecular structure candidates suitable for being associated with the one or more signal peaks; providing by one of calculating, estimating, deriving and deducing for each molecular structure candidate a distribution of first match scores as a function of mobility; defining a presumed first match score for each molecular structure candidate as output from the respective distribution on applying the experimental value of mobility of the one or more signal peaks; and using the presumed first match score in a step of associating a molecular structure with the one or more signal peaks.

20 Claims, 5 Drawing Sheets

(58) Field of Classification Search
CPC .... G01N 33/6848; G01N 21/73; G01N 21/01; G01N 21/623; G01N 2021/0112; G16C 20/20

USPC ..................................... 250/281, 282, 504 R

See application file for complete search history.

(56) References Cited

U.S. PATENT DOCUMENTS

| | | | | |
|---|---|---|---|---|
| 2006/0219896 | A1* | 10/2006 | Hashimoto | H01J 49/0027 250/288 |
| 2008/0251712 | A1* | 10/2008 | Sanders | H01J 49/004 250/282 |
| 2009/0076737 | A1* | 3/2009 | Wang | G01N 33/6848 702/23 |
| 2013/0013274 | A1* | 1/2013 | Grothe, Jr. | H01J 49/0009 703/2 |
| 2014/0045273 | A1* | 2/2014 | Cerda | G16C 20/20 422/83 |
| 2017/0250062 | A1* | 8/2017 | Green | H01J 49/0031 |
| 2020/0273545 | A1* | 8/2020 | Ryu | G16C 20/20 |

FOREIGN PATENT DOCUMENTS

| | | |
|---|---|---|
| WO | 2004111609 A2 | 12/2004 |
| WO | 2010119289 A2 | 10/2010 |
| WO | 2010119293 A3 | 10/2010 |
| WO | 2011027131 A1 | 3/2011 |
| WO | 2011128703 A1 | 10/2011 |
| WO | 2014170664 A2 | 10/2014 |
| WO | 2015040381 A1 | 3/2015 |
| WO | 2015136272 A1 | 9/2015 |
| WO | 2016142692 A1 | 9/2016 |
| WO | 2020016428 A1 | 1/2020 |

OTHER PUBLICATIONS

Henderson, Sheila C. et al., "ESI/Ion Trap/Ion Mobility/Time-of-Flight Mass Spectrometry for Rapid and Sensitive Analysis of Biomolecular Mixtures" (Anal. Chem. 1999, 71, 291-301).

Mosier, Philip D. et al., "Prediction of Peptide Ion Collision Cross Sections from Topological Molecular Structure and Amino Acid Parameters" (Anal. Chem. 2002, 74, 1360-1370).

Valentine, Stephen J. et al., "Using Ion Mobility Data to Improve Peptide Identification: Intrinsic Amino Acid Size Parameters", (J Proteome Res. May 6, 2011; 10(5) 2318-2329).

* cited by examiner

PHYSICAL-CHEMICAL PROPERTY SCORING FOR STRUCTURE ELUCIDATION IN ION SPECTROMETRY

BACKGROUND OF THE INVENTION

Field of the Invention

The disclosure relates to methods of associating molecular structures with signal peaks contained in spectrometry data which have been obtained from separation according to one or more physical-chemical properties. The spectrometry data may encompass ion spectrometry data. Ion spectrometry data may have been obtained from separation according to physical-chemical properties in the gas phase, such as ion mobility K or ion mass m or ion mass-to-charge ratio m/z. Ion spectrometry data may likewise have been obtained from separation according to physical-chemical properties before ionization and/or transfer into the gas phase, such as retention time in liquid chromatography, for example.

Description of the Related Art

The related art is explained in this introduction with reference to a specific aspect. However, this should not be understood as limiting the following disclosure of the invention. Useful developments and modifications from that which is known in the related art may also be applicable beyond the comparatively narrow scope of this introduction and will be readily apparent to skilled practitioners in the field after reading the disclosure of the invention following this introduction.

Database search algorithms to identify proteins have advanced since the SEQUEST software package was first introduced in 1994 (Jimmy K. Eng et al., J. Am. Soc. Mass Spectrom. 1994, 5, 976-989). The search engines calculate scores by comparing experimental spectra from MS/MS data against in-silico spectra derived from protein databases. Even though a lot of effort has been invested in improving protein identification, still a large number of spectra cannot be identified. One of the obstacles is spectrum ambiguity. For example, more than one peptide candidate from the protein database can often have the same precursor mass and similar fragment ion patterns generating competing peptide spectrum match search scores.

In the following, a short account of publications dealing with this established type of spectrum evaluation, without claiming completeness, will be given:

By way of example, the patent publication WO 2004/013635 A2 presents a system and method for scoring peptide matches. Embodiments comprise introducing an appropriate signal detection based scoring system, including generating a stochastic model based on one or more match characteristics associated with a first peptide, a second peptide and their fragments, to score a match between the first peptide and the second peptide. A first probability that the first peptide matches the second peptide, and a second probability that the first peptide does not match the second peptide, is calculated based on the stochastic model. And a match between the first peptide and the second peptide is scored based at least in part on a ratio between the first probability and the second probability.

By further way of example, the patent publication WO 2020/016428 A1 discloses a method for determination of identity of at least one entity from a mass spectrum of said at least one entity and optionally from additional data from chemical, physical, biochemical or biological analysis of said at least one entity, for each entity comprising the steps of: a) collecting analytical data from mass spectrum of the entity, and optionally collecting additional analytical data from a chemical, physical, biochemical or biological analysis of the entity, b) obtaining a plurality of candidate identities of the entity and obtaining the prevalences of said candidate identities of the entity, whereas for each candidate identity it applies that all candidate identities with a higher prevalence are included in the plurality of candidate identities; c) for each candidate identity of an entity, calculation of its score, said calculation involving at least prevalence of entity, or at least prevalence of entity and agreement with mass spectrum, d) determining the identity of an entity as the candidate identity with the score closest to the score which would correspond to the true identity of the entity.

In the further course of scientific development, a solution to accurately clarifying a significant number of spectra arose by adding an extra dimension of separation to the measurement cycle which heretofore usually included retention time from liquid chromatography and ion mass or mass-to-charge ratio m/z from (tandem) mass spectrometry. The extra dimension of separation is CCS (collisional cross-section) derived from ion mobility separation stages, hyphenated as the case may be with upstream and/or downstream mass separation stages and/or upstream chromatographic separation stages.

In the following, a short account of publications dealing with this type of enhanced spectrum evaluation, again without claiming completeness, will be given:

Sheila C. Henderson et al. (Anal. Chem. 1999, 71, 291-301) report an approach of identifying many different peptide sequences that have indistinguishable molecular weights with an integrated approach including the ability to resolve different sequences of oligomers by differences in their mobilities and assigning peaks based on comparisons with molecular modeling.

Philip D. Mosier et al. (Anal. Chem. 2002, 74, 1360-1370) report quantitative structure-property relationships (QSPRs) to predict the ion mobility spectrometry (IMS) collision cross sections of singly protonated lysine-terminated peptides using information derived from topological molecular structure and various amino acid parameters. The study finds that primary amino acid sequence alone would be sufficient to accurately predict the collision cross section. The models were built using multiple linear regression (MLR) and computational neural networks (CNNs).

The patent publications WO 2010/119289 A2 and WO 2010/119293 A2 each disclose a method of estimating the cross-sectional area of a molecule for use in the prediction of ion mobility giving gas phase interaction radii determination and cross-sectional algorithm computation to provide separation and characterization of structurally related isomers.

The patent publication WO 2011/027131 A1 discloses a method of screening a sample for the presence of one or more known compounds of interest. A fragmentation device is repeatedly switched between a fragmentation mode of operation and a non-fragmentation mode of operation. A determination is made whether a candidate parent ion of interest (M1) is present in a non-fragmentation data set and whether one or more corresponding fragment ions of interest (M2, M3, M4 . . . ) are present in a fragmentation data set. A further determination is made to check if the candidate parent ion of interest (M1) and the one or more corresponding fragment ions of interest (M2, M3, M4 . . . ) have substantially similar elution or retention times and/or ion mobility drift times.

Stephen J. Valentine et al. (J Proteome Res. 2011 May 6; 10(5) 2318-2329) report a scoring scheme for aiding peptide ion identification using drift times obtained from a drift tube gas phase ion mobility separator.

The patent publication WO 2011/128703 A1 discloses a method of and apparatus for identifying and/or characterizing a sample that may incorporate two or more isomeric or isobaric compounds such as hydroxylated metabolites. The method involves modelling an ensemble of possible structures for each of two or more known isomeric or isobaric compounds, calculating a theoretical collision cross-section for each modelled structure, and averaging the calculated values for each known compound to provide a theoretical collision cross-section value for each known compound. A travelling wave ion mobility cell is used to measure a collision cross-section value for the sample compound and the measured value is then compared with the theoretical values to identify which of the two or more known compounds the sample compound most closely resembles.

The patent publication WO 2014/170664 A2 discloses a method of screening a sample for at least one compound of interest. The method comprises comparing the ion mobility and at least one further physicochemical property of the ions of a compound of interest to the same properties of candidate ions in the sample. The properties of the compound of interest are matched to those of a candidate ion in the sample, then the sample is determined to comprise the compound of interest.

The patent publication WO 2015/136272 A1 discloses a method of mass spectrometry in which the collision or interaction cross sections and the masses or mass-to-charge ratios of one or more analyte ions are experimentally determined or measured, and a first list of possible candidate compounds is compiled based on the determined or measured masses or mass-to-charge ratios. A collision or interaction cross section is then theoretically calculated, estimated or determined for each candidate compound in the first list. The theoretically calculated, estimated or determined collision or interaction cross sections is then used to filter or remove candidate compounds from the first list or to reduce a likelihood value associated with one or more of the candidate compounds in the first list.

In view of the foregoing, there is still a need for an improved method of associating molecular structures with signal peaks in spectrometry data which have been obtained from separation according to one or more physical-chemical properties. Further merits and benefits of the technical teaching will be evident to a skilled person upon reading the following disclosure.

SUMMARY OF THE INVENTION

In a first aspect, the disclosure relates to a method of associating molecular structures with signal peaks (contained) in spectrometry data obtained from separation according to one or more physical-chemical properties, comprising, as the case may be repeatedly:

Providing one or more signal peaks in acquired spectrometry data being related to an experimental value of (gas phase ion) mobility or a related property;

Ascertaining one or more molecular structure candidates suitable for being associated with the one or more signal peaks;

Providing by one of calculating, estimating, deriving and deducing for each molecular structure candidate a (individual) distribution of first match scores as a function of mobility or related property;

Defining a presumed first match score for each molecular structure candidate as output from the respective distribution on applying the experimental value of mobility or related property of the one or more signal peaks; and Using the presumed first match score in a step of associating a molecular structure with the one or more signal peaks.

In various embodiments, the presumed first match score may be used to exclude a molecular structure from the associating. A landmark may be established for the first match score on a match score scale defining a first range which suggests exclusion of a molecular structure from the associating and a second range which suggests a potentially true associating.

In various embodiments, the one or more signal peaks may have one or more experimental values of a second physical-chemical property and each molecular structure candidate may be related to one or more candidate values of the second physical-chemical property. The one or more candidate values may show a level of agreement with the one or more experimental values of the second physical-chemical property, thereby implicating a second match score for each molecular structure candidate. The second match score may further be used in a step of associating a molecular structure with the one or more signal peaks. The second match score and the presumed first match score may be used separately but conjointly in a (quadratic) discriminant analysis in order to tell likely matches or identifications from unlikely matches or identifications.

In various embodiments, the presumed first match score and the second match score may be combined in order to generate a third match score. The third match score may be used in a step of associating a molecular structure with the one or more signal peaks. Preferably, a molecular structure candidate having a most extreme value of at least one of the presumed first match score, the second match score and the third match score may be taken to associate a molecular structure with the one or more signal peaks. In particular, a molecular structure candidate having the highest score of at least one of the presumed first match score, second match score and third match score may be taken to associate a molecular structure with the one or more signal peaks. Further, all molecular structure candidates having lower scores in relation to the afore-mentioned highest score(s) can be taken to not indicate a valid associating.

In various embodiments, the one or more experimental values of the second physical-chemical property and the one or more candidate values of the second physical-chemical property, which are related to each molecular structure candidate, may be indicative of molecular weights of at least one of a precursor ionic species and associated fragment ionic species of the precursor ionic species upon dissociation. Fragment ionic species may be generated by dissociating a single precursor ionic species or a plurality of fragment ionic species may be generated by simultaneously dissociating two or more precursor ionic species. In the latter case, the number of precursor ionic species being dissociated together may be controlled by the settings of a mobility separation stage and an additional mass filtering taking place between the mobility separation stage and a dissociation or fragmentation stage.

In various embodiments, separation according to the (gas phase ion) mobility or related property may at least one of precede and follow separation according to the second physical-chemical property. Preferably, separation according to the second physical-chemical property may comprise at least one of mass or mass-to-charge ratio (m/z) filtering and mass or mass-to-charge ratio dispersion, for example time-of-flight (TOF) dispersion in a flight tube. The flight tube may be substantially field-free or may contain a field-free region and a reflector. Filtering of masses or mass-to-charge ratios may in particular render information that can be used in ascertaining a subset of potential molecular structure candidates from a large host of generally available molecular structure candidates that would otherwise be impractical to process due to its sheer size, especially for a particular molecule class of interest such as peptides and proteins, and the like, where several million molecular structures are conceivable.

In various embodiments, each distribution may be configured such that it can result in first match scores that deviate from one another. Preferably, the first match scores which can result from applying the experimental or experimentally determined mobility or related property value to (or inserting it in) a distribution may deviate as a function of distance from a mobility or related property seed value of the distribution such as characterizing a distribution center or position of highest score. Each distribution may be individual, e.g. each distribution may be characterized by individual and unambiguous parameters, e.g. a seed value localizing its center or position of highest score and a width value being indicative of a fall-off rate as a function of distance from the center or position of highest score.

In various embodiments, each distribution may be configured such that it can result in a region of highest first match score and (first) adjacent region of reduced first match score in relation thereto along a mobility or related property scale. Preferably, each distribution may further be configured such that it can result in a second adjacent region of reduced first match score in relation to the region of highest first match score and first adjacent region of reduced first match score. In particular, a distribution may render three or more distinct first match scores, dependent on the localization of the experimental value of mobility or related property. Preferably, each distribution may follow an analytical function, such as a Gaussian function or other suitable mathematical function. Such mathematical function may be defined by one or more mobility or related property seed values and one or more width parameters, for example. In case of a Gaussian function the width parameter may be a sigma ($\sigma$) width or a full width at half maximum (FWHM) width. The sigma width may account for one of twenty (20) percent, fifteen (15) percent, ten (10) percent, five (5) percent and one (1) percent of the mobility or related property seed value (e.g. center value or value of highest score). The function may be substantially continuous or may be stepwise continuous. Generally, a distribution may be configured such as to show a single apex. Further, a distribution may be configured symmetric in that it has the same form or shape in either direction of the mobility or related property scale, starting from a mobility or related property seed value, such as the center value of a Gaussian function. A distribution may likewise be configured asymmetric in that it has different form or shape dependent on the direction along the mobility or related property scale, starting from a seed value. In other words, a distribution can also be skewed or distorted. It is possible that a first distribution of a first molecular structure candidate and a second distribution of a second molecular structure candidate may partially overlap.

In various embodiments, the first match score may be indicative of a probability on a scale between a first value (match excluded) and a second value (match certain). More generally, the first match score may be a scalar. In particular, the first value may equate with zero and the second value may equate with unity.

In various embodiments, the calculating, estimating, deriving or deducing may include methods of at least one of (i) statistical evaluation, (ii) machine learning and (iii) deep learning, on the basis of previously acquired and characterized spectrometry data sets. A distribution of first match scores may be representative of a standard deviation (or other parameter being indicative of reproducibility) within a plurality of existing spectrometry data sets for a particular molecular structure candidate. A distribution may likewise be representative of an estimation, regression, interpolation or extrapolation if no prior spectrometry data for a particular molecular structure candidate exist. In various embodiments, the machine or deep learning may be executed using a mixture density network (MDN) model.

In various embodiments, the one or more signal peaks may result from ionic species of biomolecular origin. Preferably, the ionic peaks may result from peptides, proteins, lipids, glycans, polysaccharides, oligonucleotides, metabolites and the like.

In various embodiments, the one or more molecular structure candidates may be ascertained from a pool of target candidates, being indicative of possible molecular structures, and a pool of decoy candidates, being indicative of impossible molecular structures. The presumed first match score may be used for defining a metric that assists in discriminating trustworthy associating and untrustworthy associating, in particular exploiting the knowledge that decoy candidate matches cannot be true.

In a second aspect, the disclosure relates to a method of associating molecular structures with signal peaks (contained) in spectrometry data obtained from separation according to one or more physical-chemical properties, comprising:

Providing a plurality of signal peak groups in acquired spectrometry data and a plurality of experimental values of (gas phase ion) mobility or a related property, each signal peak group being related to an experimental value of (gas phase ion) mobility or related property and having one or more signal peaks;

Ascertaining a plurality of molecular structure candidate groups from a pool of target candidates, being indicative of possible molecular structures, and a pool of decoy candidates, being indicative of impossible molecular structures, each molecular structure candidate group having one or more molecular structure candidates and being suitable for being associated with one or more signal peak groups;

Providing by one of calculating, estimating, deriving and deducing for each molecular structure candidate one or more candidate values of (gas phase ion) mobility or related property;

Providing a plurality of match scores by defining one or more match scores for each molecular structure candidate as a function of a level of agreement between the one or more candidate values of (gas phase ion) mobility or related property and the plurality of experimental values of (gas phase ion) mobility or related property of the plurality of signal peak groups; and Using the plurality of match scores for defining a metric that assists in discriminating trustworthy associating and untrustworthy associating.

In various embodiments, the match score may be a scalar. Preferably, the scalar may take values between zero and unity.

In various embodiments, a match score landmark may be established on a match score scale defining a first range presumed to be indicative of untrustworthy associating, regardless of whether the underlying molecular structure candidate is from the pool of decoy candidates or target candidates, and a second range presumed to be indicative of trustworthy associating.

Preferably, the match score landmark may be defined such that a percentage of less than one of five (5) percent, four (4) percent, three (3) percent, two (2) percent and one (1) percent of signal peak groups found to be associated with molecular structure candidates from the pool of decoy candidates lies in the second range.

In a third aspect, the disclosure relates to an apparatus for registering ionic species resulting from separation according to one or more physical-chemical properties, including a data processing unit designed and configured for executing methods as described hereinbefore.

BRIEF DESCRIPTION OF THE DRAWINGS

The invention can be better understood by referring to the following figures. The elements in the figures are not necessarily to scale, emphasis instead being placed upon illustrating the principles of the invention (often schematically).

DETAILED DESCRIPTION

While the invention has been shown and described with reference to a number of different embodiments thereof, it will be recognized by those skilled in the art that various changes in form and detail may be made herein without departing from the scope of the invention as defined by the appended claims.

Figure 1:
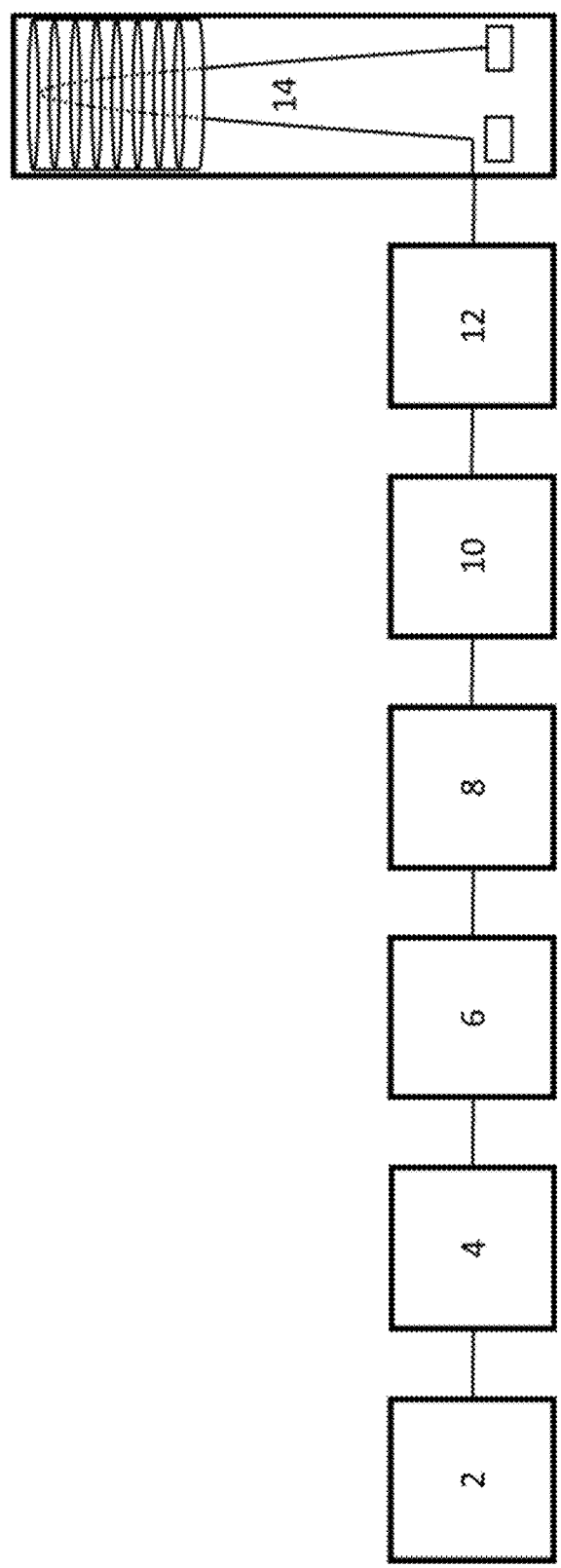
FIG. 1 depicts a schematic representation of an ion spectrometer, with which spectrometry data can be acquired that have undergone separation according to a plurality of physical-chemical properties, such as retention time, gas phase ion mobility and mass or mass-to-charge ratio.

FIG. 1 is a schematic representation of a possible ion spectrometer apparatus comprising a plurality of different separation stages with which spectrometry data dispersed according to several physical-chemical properties can be acquired.

A sample can be separated first in a chromatographic stage, as indicated at 2. The chromatographic stage may comprise a liquid chromatography stage having a column encompassing a suitable stationary phase through which the sample dissolved in a suitable mobile phase is flowed. The result may be a sequence of subsequently eluting chromatographic peaks at characteristic retention times, dependent on the chromatographic conditions set.

The eluent of the chromatographic stage can be passed on to an ion source, as indicated at 4, which may turn the sample molecules contained in the eluent peaks into gas-borne charged analyte molecules or analyte ions. The ion source may be an electrospray ion source which exploits a high voltage difference established at a spray nozzle in relation to a counter electrode to nebulize and ionize a liquid sample, such as one eluting from a liquid chromatography column. In general, ions may be generated for example by using spray ionization (e.g., electrospray (ESI) or thermal spray), desorption ionization (e.g., matrix-assisted laser/desorption ionization (MALDI) or SIMS ionization), chemical ionization (CI), photoionization (PI), electron impact ionization (EI), or gas-discharge ionization.

The analyte ions can be collected and funneled into a well collimated beam of ions facilitating their efficient transfer into an ion mobility separation stage, as indicated at 6. The ion mobility separation stage may exploit the interaction of the analyte ions with a moving or stagnant gas while being acted upon by an electric field, either held constant or varied over time. By way of example, the ion mobility separation stage may be designed and configured according to the principles of trapped ion mobility separation (TIMS). The disclosure U.S. Pat. No. 7,838,826 B1, which is incorporated herein by reference in its entirety, gives examples of TIMS separation stages. The result of ion mobility separation may be a sequence of subsequently eluting ionic mobility peaks at characteristic times, dependent on the conditions of the mobility separation set. Other suitable types of gas phase ion mobility separators may encompass drift tube ion mobility separators (DTIMS), travelling wave ion mobility separators (TWIMS), or gas phase ion mobility filters like field asymmetric ion mobility separators (FAIMS).

The eluted mobility peaks can pass an ion guide stage, as indicated at 8, which may serve to pass the analyte ions through a pressure differential between comparatively high pressure in the ion mobility separation stage and lower pressure maintained in the subsequent stages for further gas phase ion handling and manipulation. Such ion guide stage may encompass various ion guides, e.g. multipole rod set ion guides and or stacked ring ion guides.

A filter stage, as indicated at 10, can follow the ion guide stage. The filter stage may comprise a mass filter such as a quadrupole mass filter that facilitates transmission of analyte ions in a broadband or precursor screening mode, which aims at sorting out as few ions as possible or in other words transmits as many of the incoming ions as possible, and one of a bandpass filter mode, highpass filter mode and lowpass filter mode, the aim of which is to reduce a transmission window to a comparatively narrow mass or mass-to-charge ratio (m/z) range, thereby entailing dismissing ions not falling in this transmission window. The broadband or precursor screening mode and any one of the filter modes may be alternated in (quick) succession.

A fragmentation stage, as indicated at 12, can follow the filter stage. The fragmentation stage may comprise an ion guide filled with a collision gas and further be equipped with electrodes which facilitate the switching of an acceleration voltage for pulling analyte ions at high speed into the collision gas in order to induce dissociation. Precursor ions selected from the analyte ions can be fragmented into a plurality of characteristic fragment ions. In general, ions can for example be fragmented in the fragmentation stage by collision induced dissociation (CID), surface induced dissociation (SID), photo-dissociation (PD), electron capture dissociation (ECD), electron transfer dissociation (ETD), collisional activation after electron transfer dissociation (ETcD), activation concurrent with electron transfer dissociation (AI-ETD) or fragmentation by reactions with highly excited or radical neutral particles.

The ions emanating from the collision cell can be passed on to a mass separation stage, as indicated at 14. The mass separation stage may take the form of a reflector time-of-flight (rTOF) separation stage featuring orthogonal ion injection into the time-of-flight flight tube. At the end of the curved flight path within the flight tube the ions may be registered by an impact detector, such as a secondary electron multiplier detector. The result may be a spectrum that plots ion abundance, such as ion intensity, over a molecular weight or mass-related scale, such as the time of flight. Together with the information from the chromatographic stage 2 and the ion mobility separation stage 6, the spectrometry data can be presented in different maps, such as 3D plots where each axis corresponds to a scale of the physical-chemical properties (i) retention time from the chromatographic stage 2, (ii) gas phase ion mobility or related property from the ion mobility separation stage 6, and (iii) mass or mass-to-charge ratio or related property from the mass separation stage 14, while the abundance of signal peaks can be represented by color or another suitable graphical feature.

Figure 2:
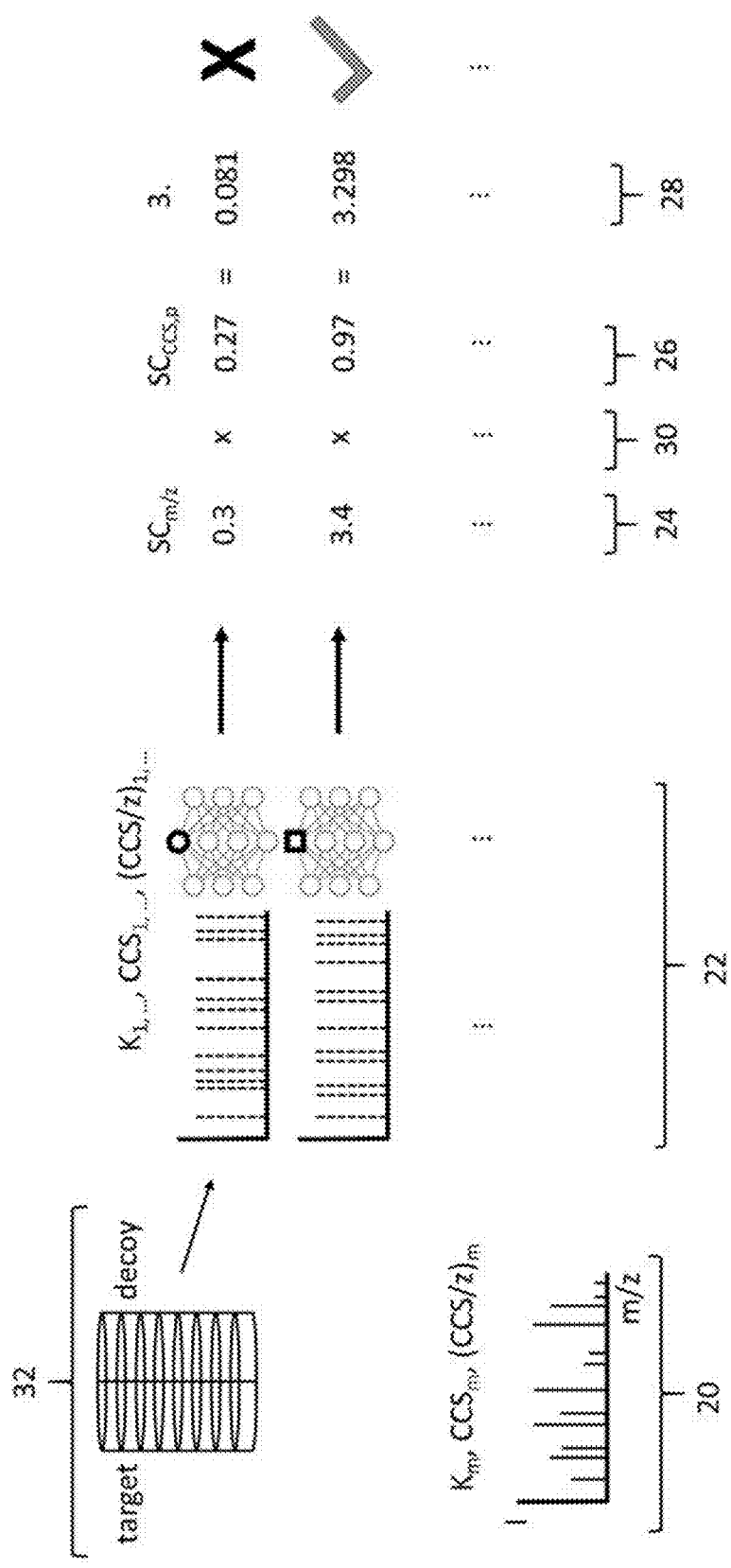
FIG. 2 schematically shows various steps in a structure identification workflow applied to spectrometry data such as resulting from an apparatus as depicted in FIG. 1.

FIG. 2 shows schematically a method of associating molecular structures with signal peaks contained in spectrometry data obtained from separation according to one or more physical-chemical properties, such as exemplified with reference to FIG. 1, in several steps.

First, one or more signal peaks in acquired spectrometry data such as a spectrum are provided, as indicated on the left of the figure at 20. The one or more signal peaks may result from ionic species of biomolecular origin such as peptides, proteins, lipids, glycans, polysaccharides, oligonucleotides, metabolites and the like. The spectrometry data may be related to an experimental or experimentally determined value of gas phase ion mobility $K_m$ or a related property, such as resulting from separation in an ion mobility separation stage 6 in FIG. 1. The related property may encompass, for example, a proxy such as the drift time $t_{D,m}$ of an ionic species through a drift tube ion mobility separator or a derived or deduced parameter such as the collision cross section $CCS_m$ (proportional to 1/K) or the collision cross section-to-charge ratio $(CCS/z)_m$.

One or more molecular structure candidates suitable for being associated with the one or more signal peaks may be ascertained. The ascertaining may be based on a mass or mass-to-charge ratio filtering, such as using a quadrupole mass filter, during the acquisition of the spectrometry data in order to define a finite mass or mass-to-charge ratio range with which the candidates have to conform, such as resulting from a filter stage 10 in FIG. 1. The one or more signal peaks may have a plurality of experimental values of a second physical-chemical property, and each molecular structure candidate may be related to one or more candidate values of the second physical-chemical property, as indicated in the figure at 22. The one or more experimental values of the second physical-chemical property and the one or more candidate values of the second physical-chemical property, which are associated with each molecular structure candidate, may be indicative of molecular weights of at least one of a precursor ionic species and associated fragment ionic species of the precursor ionic species upon dissociation. Preferably, the second physical-chemical property may encompass ion mass m or ion mass-to-charge ratio m/z. It is also possible that the second physical-chemical property may encompass a proxy of ion mass m such as time of flight in a flight tube of a time-of-flight separator.

In a matching step, the one or more candidate values may show a level of agreement with the one or more experimental values of the m/z or related property, thereby implicating an m/z or related property match score $SC_{m/z}$ for each molecular structure candidate, as indicated in the figure at 24. Further, the m/z or related property match score $SC_{m/z}$ may be used in a step of associating a molecular structure with the one or more signal peaks. The m/z or related property match score $SC_{m/z}$ may be a scalar and may be calculated by adding up unity every time an m/z or related property value of the one or more signal peaks agrees with, or falls in the same m/z or related property bin as a candidate m/z or related property value of the molecular structure candidate under examination. The more signal peaks there are to be subjected to matching, the higher the m/z or related property match score $SC_{m/z}$ may become. In such algorithm, the higher the m/z or related property match score $SC_{m/z}$ is, the more trustworthy an identification result may become.

The order of separation according to one or more physical-chemical properties may be set such that separation according to the (gas phase ion) mobility or related property at least one of precedes and follows separation according to the m/z or related property. For example, separation according to the m/z or related property may comprise at least one of mass or mass-to-charge ratio filtering and mass or mass-to-charge ratio dispersion, such as time-of-flight dispersion in a flight tube, both being executed by way of example after separation according to the mobility or related property, as explained with reference to the schematic in FIG. 1.

Figure 3A:
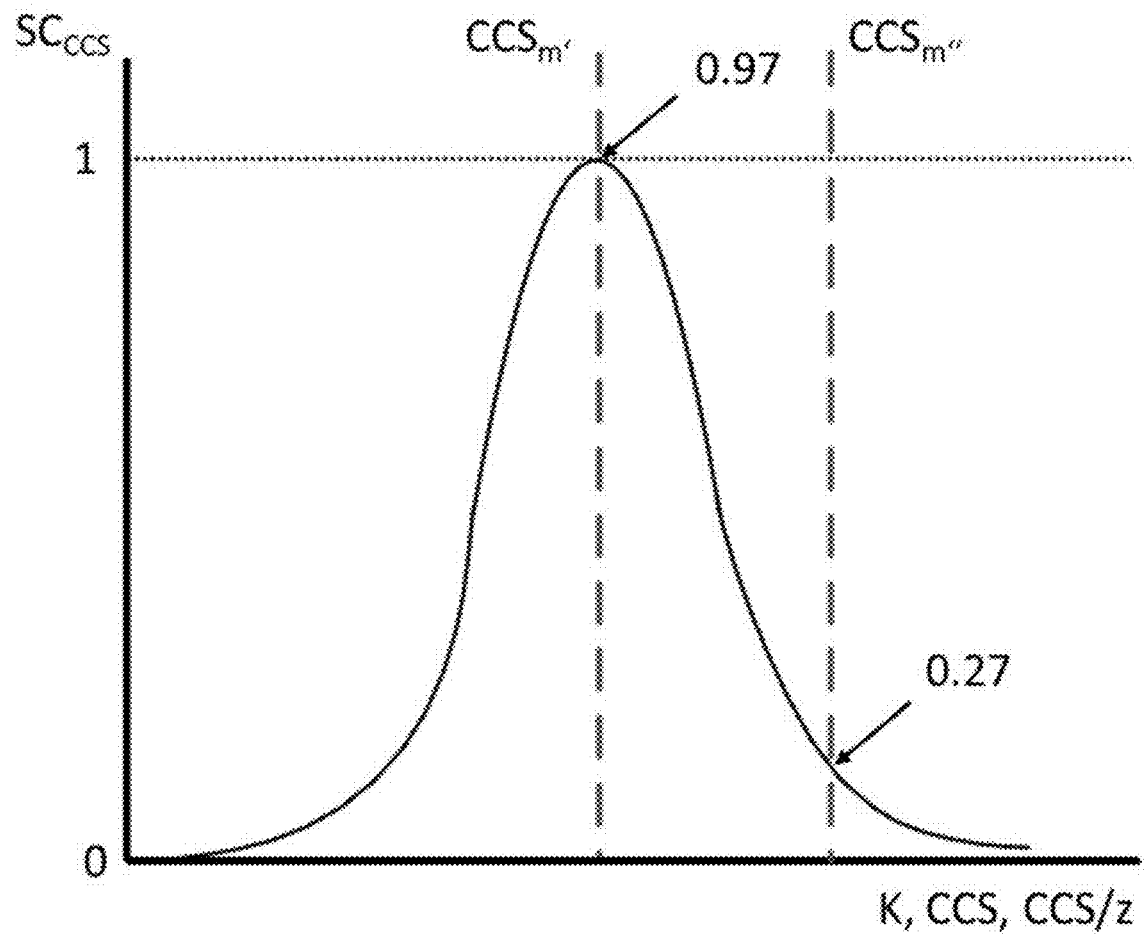
FIG. 3A illustrates a match score distribution for a molecular structure candidate.

For each molecular structure candidate, an individual distribution of mobility or related property match scores $SC_{CCS}$ as a function of mobility or related property may be provided by one of calculating, estimating, deriving or deducing, as shown in FIG. 3A. The calculating, estimating, deriving or deducing may include methods of at least one of (i) statistical evaluation, (ii) machine learning and (iii) deep learning, on the basis of previously acquired and characterized spectrometry data sets. Each distribution may be characterized by one or more mobility or related property seed values, such as defining a center of a distribution or a position of highest score. The mobility or related property match score $SC_{CCS}$ may be indicative of a probability on a scale between a first value (match excluded) and a second value (match certain). The first value may be zero and the second value may be unity, as shown. Each distribution may be configured such that it can result in mobility or related property match scores $SC_{CCS}$ that deviate from one another. Preferably, each distribution may be configured such that it can result in a region of highest mobility or related property match score $SC_{CCS}$ along a mobility or related property scale, such as indicated at the position close to the center of the distribution rendering a value of 0.97 (first vertical dashed line), and adjacent region of reduced mobility or related property match score $SC_{CCS}$ in relation thereto, such as indicated on the falling flank of the distribution rendering a value of 0.27 (second vertical dashed line). There may be more regions of deviating mobility or related property match scores along the course of a distribution, as evident.

Each distribution may follow an analytical function such as a Gaussian function or other suitable mathematical function, e.g. a stepwise function or stepwise continuous function, that is representative of a probability-weighted deviation or spreading of previously observed or experimentally determined mobility or related property values for the molecular structure candidate under examination. A distribution may also be representative of an estimation, derivation and/or deduction of mobility or related property match scores for molecular structure candidates for which no prior spectrometric data exist, in particular by exploiting methods of deep learning and/or machine learning on existing data sets. In various embodiments, the machine or deep learning may be executed using mixture density network (MDN) models.

Figure 3B:
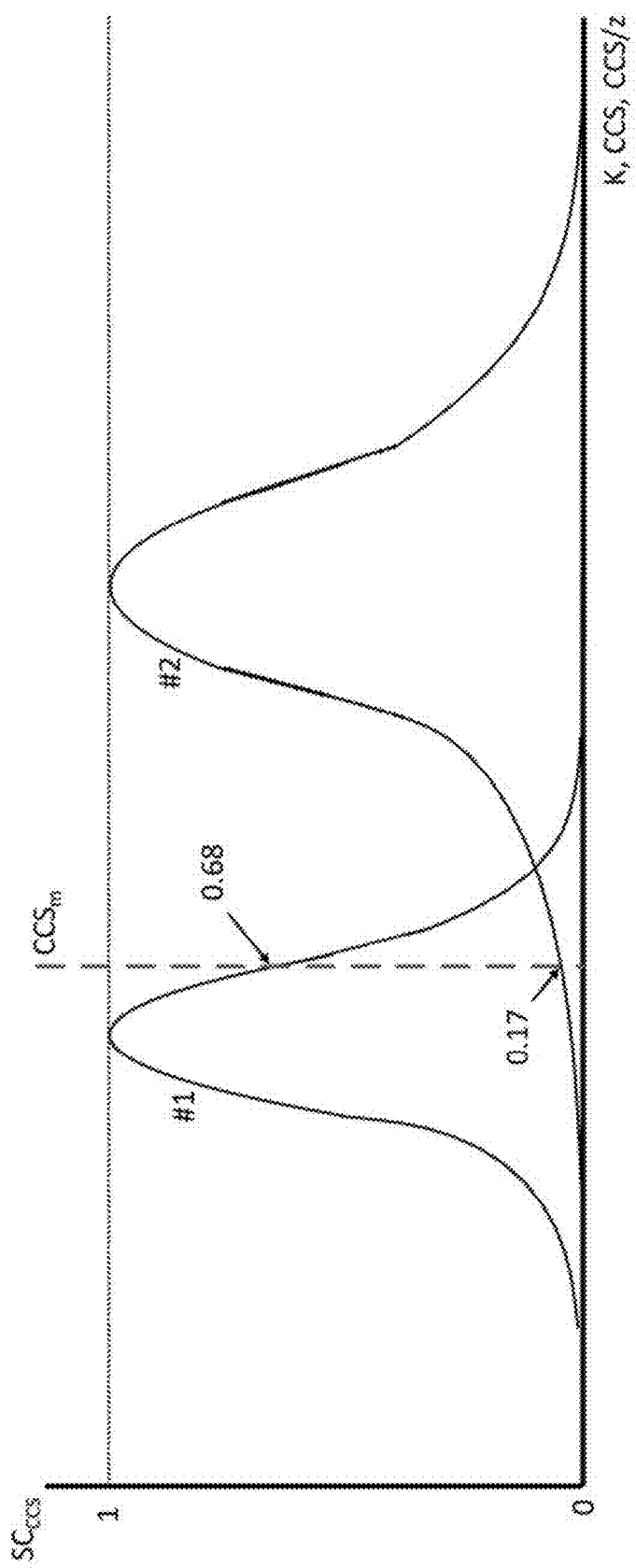
FIG. 3B shows two partially overlapping match score distributions for two molecular structure candidates.

It is possible that a first distribution of a first molecular structure candidate and a second distribution of a second molecular structure candidate partially overlap, such as shown exemplarily in FIG. 3B. This may entail that a presumed mobility or related property match score $SC_{CCS,p}$ results higher in the case of a first molecular structure candidate, higher up the falling flank in the left distribution #1 yielding 0.68, than in case of another competing molecular structure candidate, further down the rising flank in the right distribution #2 yielding 0.17, rendering a further factor to be considered in the judgement of the matching and allowing increasing the match quality. In the example shown in FIG. 3B, this could be interpreted that an associating of the one or more signal peaks in the spectrometry data under examination with the molecular structure candidate of distribution #1 is more trustworthy than that with the molecular structure candidate of distribution #2.

As illustrated in the FIGS. 3A and 3B, a presumed mobility or related property match score $SC_{CCS,p}$ may be defined for each molecular structure candidate as output from the respective distribution on applying or inserting the experimental or experimentally determined value of mobility or related property $CCS_m$ (or $K_m$ or $(CCS/z)_m$) of the one or more signal peaks. In other words, a presumed mobility or related property match score $SC_{CCS,p}$ may be defined for each molecular structure candidate as a function of where the experimental value of mobility or related property $CCS_m$ of the one or more signal peaks comes to lie within the mobility or related property distribution of the molecular structure candidate under examination. This is exemplified in the two vertical dashed lines in FIG. 3A, showing one experimental mobility or related property value falling into the candidate mobility or related property distribution close to the center thus resulting in a high confidence presumed match score (0.97) and one falling into the candidate mobility or related property distribution further away from the center and thus resulting in a lower confidence presumed match score (0.27).

Another example is evident from the single vertical dashed line in FIG. 3B, showing a single experimental mobility or related property value falling within a first candidate mobility or related property distribution #1 closer to the center thus resulting in high confidence, left distribution #1 at $SC_{CCS,p}$=0.68, and at the same time falling within a second competing candidate mobility or related property distribution #2 further away from its center and thus resulting in low confidence, right distribution #2 at $SC_{CCS,p}$=0.17. This finding would suggest that the molecular structure candidate associated with the left distribution #1 is the likelier or more trustworthy match than the molecular structure candidate related to the right distribution #2.

Turning back to FIG. 2, the presumed mobility or related property match score $SC_{CCS,p}$, as indicated in the figure at 26, may be used in a step of associating a molecular structure with the one or more signal peaks. In a first variant, the presumed mobility or related property match score $SC_{CCS,p}$ may be used to exclude a molecular structure from the associating. In FIG. 2, low values of the presumed mobility or related property match score $SC_{CCS,p}$ may indicate that the underlying molecular structure does not fit well the observed signal peaks in the spectrometry data 20. A landmark value of the mobility or related property match score $SC_{CCS}$ may be established defining a first range on a match score scale for dismissing molecular structures as inapplicable and a second range for accepting molecular structures as potentially true.

In one embodiment, the presumed mobility or related property match score $SC_{CCS,p}$ may be used separately and conjointly with the m/z or related property match score $SC_{m/z}$ (and further match or score parameters such as deduced or derived from retention time, intensities of fragment ionic species, isotopic distribution of ionic species, charge state of ionic species, and the like) for performing a (quadratic) discriminant analysis for telling trustworthy matches from untrustworthy matches.

In further embodiments, the presumed mobility or related property match score $SC_{CCS,p}$ and the m/z or related property match score $SC_{m/z}$ may be combined in order to generate a third match score, as indicated at 28, and the third match score may be used in a step of associating a molecular structure with the one or more signal peaks. The combining may encompass a multiplication or other suitable mathematical operation of the presumed mobility or related property match score $SC_{CCS,p}$ and the m/z or related property match score $SC_{m/z}$, as indicated at 30. A molecular structure candidate having a most extreme value of at least one of the mobility or related property match score $SC_{CCS}$, the m/z or related property match score $SC_{m/z}$ and the third match score may be taken to associate a molecular structure with the one or more signal peaks. Preferably, the highest match score of at least one of the m/z or related property match score $SC_{m/z}$, the presumed mobility or related property match score $SC_{CCS,p}$ and the third match score may indicate an associating of the one or more signal peaks with a molecular structure candidate as potentially true.

The one or more molecular structure candidates may be ascertained from a pool of target candidates, being indicative of possible molecular structures, and a pool of decoy candidates, being indicative of impossible molecular structures, as indicated at 32 in FIG. 2. The presumed mobility or related property match score $SC_{CCS,p}$ may be used for defining a metric that assists in discriminating trustworthy associating and untrustworthy associating. Using this additional information derived in particular from ion mobility separation, the calculation of a false discovery rate (FDR) or decoy hit rate (DHR) can be made more accurate.

Figure 4:
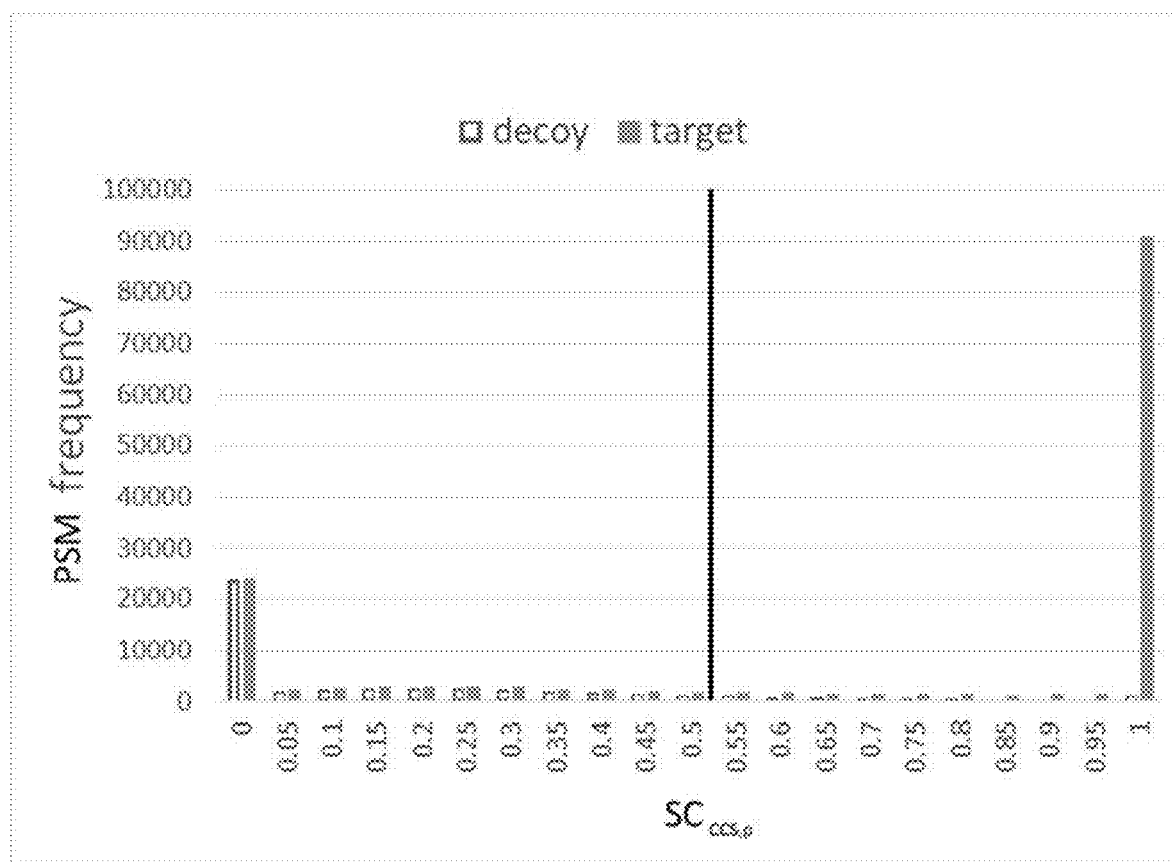
FIG. 4 shows an exemplary plot of spectrum match frequency, here on the example of peptides, as a function of presumed collision cross section match score.

FIG. 4 illustrates by way of example a plot showing peptide spectrum match (PSM) frequency on the vertical axis (y axis) as a function of presumed collision cross section match score $SC_{CCS,p}$ on the horizontal axis (x axis) for both target candidate matches (solid columns) as well as decoy candidate matches (hollow columns). As can be seen, at high match scores close to unity the target candidate matches prevail by far whereas at low match scores the frequency is spread almost equally between target candidate matches and decoy candidate matches. As it is known that the decoy candidate matches cannot be true whereas there always remains at least a modicum of uncertainty of whether a target candidate match is true, in particular in automated processing when results are not scrutinized by a seasoned practitioner, the information from the decoy candidate matches can be used in a statistical approach to define a landmark on a match score scale defining a first range of match scores that due to their low confidence will be treated as untrustworthy, regardless of whether they are decoy or target candidate matches, and a second range in which candidate matches can be treated as potentially or most likely true.

This is indicated by way of example by a solid vertical line in FIG. 4 at a match score of about 0.5. To the left of this landmark 0.5) matches can be taken as untrustworthy whereas to the right of this landmark (>0.5) matches can be presumed to be trustworthy or likely true. The landmark may be chosen such and shifted as the desired level of confidence suggests. The landmark may be chosen such that only a certain low percentage of decoy candidate matches comes to lie in the range indicating trustworthiness (right range, higher scores), such as five percent of the total number of matches, or less. This additional mobility-related metric can be used advantageously in the calculation of a false discovery rate or decoy hit rate, for instance.

The invention has been shown and described above with reference to a number of different embodiments thereof. It will be understood, however, by a person skilled in the art that various aspects or details of the invention may be changed, or various aspects or details of different embodiments may be arbitrarily combined, if practicable, without departing from the scope of the invention. Generally, the foregoing description is for the purpose of illustration only, and not for the purpose of limiting the invention which is defined solely by the appended claims, including any equivalent implementations, as the case may be.

The invention claimed is:

1. A method of associating molecular structures with signal peaks in spectrometry data obtained from separation according to one or more physical-chemical properties, comprising:
providing one or more signal peaks in acquired spectrometry data being related to an experimental value of mobility or a mobility-related property taken from a group including: collision cross section, collision cross section to charge ratio, and drift time of an ionic species through a drift tube ion mobility separator;
ascertaining one or more molecular structure candidates suitable for being associated with the one or more signal peaks;
providing by one of calculating, estimating, deriving and deducing for each molecular structure candidate a distribution of first match scores as a function of mobility or the mobility-related property, each distribution being configured such that it results in a region of highest first match score and first adjacent region of reduced first match score in relation thereto along a mobility or mobility-related property scale, wherein each distribution is further configured such that it results in a second adjacent region of reduced first match score in relation to the region of highest first match score and first adjacent region of reduced first match score;
defining a presumed first match score for each molecular structure candidate as output from the respective distribution on applying the experimental value of mobility or the mobility-related property of the one or more signal peaks; and
using the presumed first match score in a step of associating a molecular structure with the one or more signal peaks.

2. The method of claim 1, wherein the presumed first match score is used to exclude a molecular structure from the associating.

3. The method of claim 1, wherein the one or more signal peaks have one or more experimental values of a second physical-chemical property and each molecular structure candidate is related to one or more candidate values of the second physical-chemical property, the one or more candidate values showing a level of agreement with the one or more experimental values of the second physical-chemical property, thereby implicating a second match score for each molecular structure candidate, further including using the second match score in a step of associating a molecular structure with the one or more signal peaks.

4. A method of associating molecular structures with signal peaks in spectrometry data obtained from separation according to one or more physical-chemical properties, comprising:
providing one or more signal peaks in acquired spectrometry data being related to an experimental value of mobility or a mobility-related property taken from a group including: collision cross section, collision cross section to charge ratio, and drift time of an ionic species through a drift tube ion mobility separator;
ascertaining one or more molecular structure candidates suitable for being associated with the one or more signal peaks;
providing by one of calculating, estimating, deriving and deducing for each molecular structure candidate a distribution of first match scores as a function of mobility or the mobility-related property;
defining a presumed first match score for each molecular structure candidate as output from the respective distribution on applying the experimental value of mobility or the mobility-related property of the one or more signal peaks; and
using the presumed first match score in a step of associating a molecular structure with the one or more signal peaks,
wherein the one or more signal peaks have one or more experimental values of a second physical-chemical property and each molecular structure candidate is related to one or more candidate values of the second physical-chemical property, the one or more candidate values showing a level of agreement with the one or more experimental values of the second physical-chemical property, thereby implicating a second match score for each molecular structure candidate, further including using the second match score in a step of associating a molecular structure with the one or more signal peaks, the method further including combining the presumed first match score and the second match score in order to generate a third match score and using the third match score in a step of associating a molecular structure with the one or more signal peaks.

5. The method of claim 4, wherein a molecular structure candidate having a most extreme value of at least one of the presumed first match score, second match score and third match score associates a molecular structure with the one or more signal peaks.

6. The method of claim 3, wherein the one or more experimental values of the second physical-chemical property and the one or more candidate values of the second physical-chemical property, which are related to each molecular structure candidate, are indicative of molecular weights of at least one of a precursor ionic species and associated fragment ionic species of the precursor ionic species upon dissociation.

7. The method of claim 3, wherein separation according to the mobility or the mobility-related property at least one of precedes and follows separation according to the second physical-chemical property.

8. The method of claim 3, wherein separation according to the second physical-chemical property comprises at least one of mass or mass-to-charge ratio filtering and mass or mass-to-charge ratio dispersing.

9. The method of claim 1, wherein each distribution is configured such that it can result in first match scores that deviate from one another.

10. The method of claim 1, wherein each distribution follows an analytical function.

11. The method of claim 10, wherein a first distribution of a first molecular structure candidate and a second distribution of a second molecular structure candidate partially overlap.

12. The method of claim 1, wherein the first match score is indicative of a probability on a scale between a first value (match excluded) and a second value (match certain).

13. The method of claim 1, wherein the calculating, estimating, deriving or deducing includes methods of at least one of (i) statistical evaluation, (ii) machine learning and (iii) deep learning, on the basis of previously acquired and characterized spectrometry data sets.

14. The method of claim 1, wherein the one or more signal peaks result from ionic species of biomolecular origin.

15. A method of associating molecular structures with signal peaks in spectrometry data obtained from separation according to one or more physical-chemical properties, comprising:
  providing one or more signal peaks in acquired spectrometry data being related to an experimental value of mobility or a mobility-related property taken from a group including: collision cross section, collision cross section to charge ratio, and drift time of an ionic species through a drift tube ion mobility separator;
  ascertaining one or more molecular structure candidates suitable for being associated with the one or more signal peaks;
  providing by one of calculating, estimating, deriving and deducing for each molecular structure candidate a distribution of first match scores as a function of mobility or the mobility-related property;
  defining a presumed first match score for each molecular structure candidate as output from the respective distribution on applying the experimental value of mobility or the mobility-related property of the one or more signal peaks; and
  using the presumed first match score in a step of associating a molecular structure with the one or more signal peaks, the method further including ascertaining the one or more molecular structure candidates from a pool of target candidates, being indicative of possible molecular structures, and a pool of decoy candidates, being indicative of impossible molecular structures, and using the presumed first match score for defining a metric that assists in discriminating trustworthy associating and untrustworthy associating.

16. A method of associating molecular structures with signal peaks in spectrometry data obtained from separation according to one or more physical-chemical properties, comprising:
  providing a plurality of signal peak groups in acquired spectrometry data and a plurality of experimental values of mobility or a mobility-related property taken from a group including: collision cross section, collision cross section to charge ratio, and drift time of an ionic species through a drift tube ion mobility separator, each signal peak group being related to an experimental value of mobility or the mobility-related property and having one or more signal peaks;
  ascertaining a plurality of molecular structure candidate groups from a pool of target candidates, being indicative of possible molecular structures, and a pool of decoy candidates, being indicative of impossible molecular structures, each molecular structure candidate group having one or more molecular structure candidates and being suitable for being associated with one or more signal peak groups;
  providing by one of calculating, estimating, deriving and deducing for each molecular structure candidate one or more candidate values of mobility or the mobility-related property;
  providing a plurality of match scores by defining one or more match scores for each molecular structure candidate as a function of a level of agreement between the one or more candidate values of mobility or the mobility-related property and the plurality of experimental values of mobility or the mobility-related property of the plurality of signal peak groups; and
  using the plurality of match scores for defining a metric that assists in discriminating trustworthy associating and untrustworthy associating.

17. The method of claim 16, wherein the match score is a scalar.

18. The method of claim 16, further including establishing a match score landmark on a match score scale defining a first range presumed to be indicative of untrustworthy associating, regardless of whether the underlying molecular structure candidate is from the pool of decoy candidates or target candidates, and a second range presumed to be indicative of trustworthy associating.

19. The method of claim 18, wherein the match score landmark is defined such that a percentage of less than one of five percent, four percent, three percent, two percent and one percent of signal peak groups found to be associated with molecular structure candidates from the pool of decoy candidates lies in the second range.

20. An apparatus for registering ionic species resulting from separation according to one or more physical-chemical properties, including a data processing unit designed and configured for executing a method according to claim 1.

* * * * *